United States Patent [19]

Dusza et al.

[11] Patent Number: 4,654,347

[45] Date of Patent: * Mar. 31, 1987

[54] ARYL AND HETEROARYL[[7-(3-DISUBSTITUTED AMINO)PHENYL]PYRAZOLO[1,5-A]PYRIMIDIN-3-YL]METHANONES

[75] Inventors: John P. Dusza, Nanuet, N.Y.; Andrew S. Tomcufcik, Old Tappan, N.J.; Jay D. Albright, Nanuet, N.Y.

[73] Assignee: American Cyanamid Company, Stamford, Conn.

[*] Notice: The portion of the term of this patent subsequent to Jun. 4, 2002 has been disclaimed.

[21] Appl. No.: 732,985

[22] Filed: May 13, 1985

Related U.S. Application Data

[63] Continuation-in-part of Ser. No. 612,812, May 24, 1984, Pat. No. 4,521,422, which is a continuation-in-part of Ser. No. 506,966, Jun. 23, 1983, abandoned.

[51] Int. Cl.⁴ .................. A61K 31/505; C07D 471/02
[52] U.S. Cl. .................................... 514/258; 544/281
[58] Field of Search ......................... 544/281; 514/258

[56] References Cited

U.S. PATENT DOCUMENTS

| | | | |
|---|---|---|---|
| 4,178,449 | 12/1979 | Dusza et al. | 544/281 |
| 4,236,005 | 11/1980 | Dusza et al. | 544/281 |
| 4,281,000 | 7/1981 | Dusza et al. | 544/281 |
| 4,521,422 | 6/1985 | Dusza et al. | 544/281 |

Primary Examiner—Donald G. Daus
Assistant Examiner—S. Kapner
Attorney, Agent, or Firm—Susan H. Rauch

[57] ABSTRACT

Novel aryl and heteroaryl[7-(3-substituted amino phenyl)-pyrazolo[1,5-a]pyrimidin-3-yl]methanones useful as anxiolytic, antiepileptic and sedative-hypnotic agents and as skeletal muscle relaxants, methods of using the novel compounds, compositions containing them and processes for this production.

15 Claims, No Drawings

ARYL AND HETEROARYL[[7-(3-DISUBSTITUTED AMINO)PHENYL]PYRAZOLO[1,5-A]PYRIMIDIN-3-YL]METHANONES

CROSS REFERENCE TO RELATED APPLICATIONS

This application is a continuation-in-part of our co-pending application, U.S. Ser. No. 612,812, filed May 24, 1984, U.S. Pat. No. 4,521,422, which is a continuation-in-part of U.S. Ser. No. 506,966, filed June 23, 1983, now abandoned.

SUMMARY OF THE INVENTION

This invention relates to new organic compounds which are aryl or heteroaryl[[7-(3-disubstituted amino)-phenyl]pyrazolo[1,5-a]pyrimidin-3-yl]methanones which are useful as anxiolytic and antiepileptic agents, sedative-hypnotic agents and skeletal muscle relaxants. This invention also relates to the methods of using these novel compounds, to compositions of matter containing them as the active ingredient and to processes for their production.

DETAILED DESCRIPTION OF THE INVENTION

In accordance with this invention, the novel compounds are reprsented by the following structural formula:

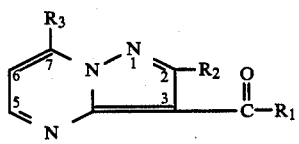

wherein
$R_1$ is selected from the group consisting of unsubstituted phenyl; phenyl mono- or disubstituted by halogen, alkyl($C_1$-$C_3$) or alkoxy($C_1$-$C_3$); phenyl monosubstituted by trifluoromethyl, alkylthio($C_1$-$C_3$), alkylamino($C_1$-$C_3$), dialkylamino($C_1$-$C_3$), methylenedioxy, alkylsulfonyl($C_1$-$C_3$) or alkanoylamino($C_1$-$C_3$); naphthalenyl; thiazolyl; biphenyl; thienyl; furanyl; pyridinyl; substituted thiazolyl; substituted biphenyl; substituted thienyl; and substituted pyridinyl, wherein the substituents are selected from one or two of the groups consisting of halogen, alkyl($C_1$-$C_3$) and alkoxy($C_1$-$C_3$);
$R_2$ is selected from the group consisting of hydrogen and alkyl($C_1$-$C_3$);
$R_3$ is

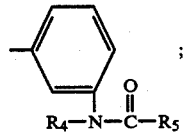

$R_4$ is selected from the group consisting of hydrogen, alkenyl($C_2$-$C_6$), —$CH_2C\equiv CH$, cycloalkyl($C_3$-$C_6$-)methyl, —$CH_2OCH_3$ and —$CH_2CH_2OCH_3$; and
$R_5$ is selected from the group consisting of hydrogen, cycloalkyl($C_{3-6}$), —O-alkyl($C_1$-$C_6$), —NH-alkyl($C_1$-$C_3$), —N-dialkyl($C_1$-$C_3$), —$(CH_2)_n$—O—alkyl($C_1$-$C_3$), —$(CH_2)_n$—NH—alkyl($C_1$-$C_3$), —$(CH_2)_n$—N-dialkyl($C_1$-$C_3$), where n is an integer 1-3 inclusive, and $R_5$ may be alkyl($C_1$-$C_6$), when $R_4$ is not hydrogen.

The most preferred compounds of the invention are those compounds of the above formula wherein $R_1$ is unsubstituted phenyl; phenyl monosubstituted by halogen, alkyl($C_1$-$C_3$), alkoxy($C_1$-$C_3$) or trifluoromethyl; thienyl; furanyl; or pyridinyl; $R_2$ is hydrogen; $R_4$ is alkenyl($C_2$-$C_6$) or —$CH_2\equiv CH$; and $R_5$ is cycloalkyl($C_3$-$C_6$), —O-alkyl($C_1$-$C_6$) or —N-dialkyl($C_1$-$C_3$). In addition, when $R_4$ is not hydrogen, $R_5$ may preferably be alkyl ($C_1$-$C_6$).

The instant invention is additionally concerned with the methods of employing the above-described compounds in mammals to treat anxiety and epilepsy and to induce a sedative-hypnotic effect or to relax skeletal muscles, with compositions of matter containing these compounds, and with processes for their production.

Details of the preparative scheme are fully apparent from the disclosure U.S. Pat. No. 4,521,422, which is hereby incorporated by reference.

The novel compounds of this invention may be readily prepared as set forth in the following reaction scheme:

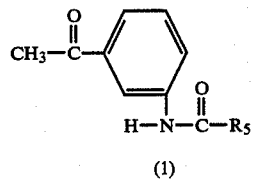

(1)

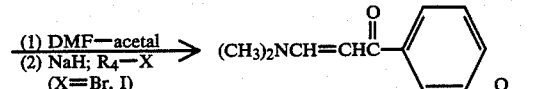

(2)

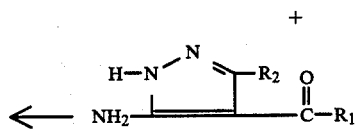

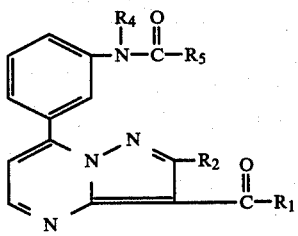

In accordance with the above reaction scheme a 1-acetylphenyl-3-amide (1), where $R_5$ is as described above, is reacted with dimethylformamide dimethylcetal at reflux, giving an N-[3-[3-(dimethylamino)-1-oxo-2-propenyl]phenyl]-alkanamide, which is then reacted with sodium hydride and the anion generated is reacted with and an alkyl halide, where $R_4$ is as described above, giving the N-[3-[3-(dimethylamino)-1-oxo-2-propenyl]phenyl]-N-alkylalkanamide (2). This compound is then reacted with a 3-aminopyrazole (3), where $R_1$ and $R_2$ are as described above, in glacial acetic acid at reflux giving the product (4).

Alternatively, an N-[3-[3-(dialkylamino)-1-oxo-2-propenyl]phenyl]alkanamide (5) is reacted with a 3-aminopyrazole (3) to give intermediates (6) which are reacted with a base such as sodium hydride, sodium alkoxide and the like and an $R_4$-halide to give the products (4).

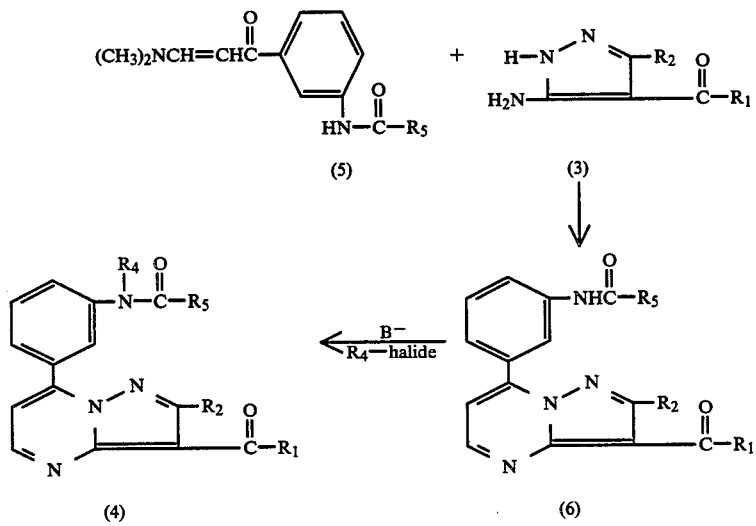

The performance of the novel compounds of the present invention in standard tests with laboratory animals which are known to correlate well with relief of anxiety in man indicates that they possess central nervous system activity at nontoxic doses and as such are useful as anxiolytic agents. Furthermore, these compounds have been shown by biological data to be useful as antiepileptic agents, particularly in the treatment of grand mal seizures, and as sedative-hypnotic and skeletal muscle relaxant agents.

The anti-anxiety and anticonvulsant properties of the novel compounds of the present invention have been established in a test which indicates anxiolytic and antiepileptic activity by the measure of protection from convulsions resulting from the administration of pentylenetetrazole. Single or graded dose levels of the test compounds were administered orally or intraperitoneally in a 2% starch vehicle, containing 0.5% v/v polyethylene glycol and one drop of Polysorbate 80 to groups of at least 4 rats. At 30 or 60 minutes, the rats were treated intravenously with pentylenetetrazole at a dose of 23 mg/kg of body weight. This dose is estimated to cause clonic seizures in 99% of unprotected rats. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, pp 237-288 (1971)] that there is a high degree of correlation between the ability of compounds to inhibit the seizure-inducing effect of pentylenetetrazole in rats and the effectiveness of those compounds as anxiolytic and anticonvulsive agents in higher warm-blooded animals. The results of this test on representative compounds of the present invention are shown in Table I.

TABLE I

| Compound | Dose (mg/kg) | % of Rats Protected |
|---|---|---|
| Protection Against Clonic Seizures Caused by Pentylenetetrazole in Rats | | |
| [3-[3-(2-furanylcarbonyl)pyrazolo-[1,5-a]pyrimidin-7-yl]phenyl]methylcarbamic acid, methyl ester | 3.1 | 75 |
| [3-(3-benzoylpyrazolo[1,5-a]pyrimidin-7-yl)phenyl]methylcarbamic acid, methyl ester | 12.5 | 100 |
| [3-(3-benzoylpyrazolo[1,5-a]pyrimidin-7-yl)phenyl]ethylcarbamic acid, methyl ester | 12.5 | 100 |
| ethyl[3-[3-(2-furanylcarbonyl)pyrazolo[1,5-a]pyrimidin-7-yl]phenyl]carbamic acid, methyl ester | 6.25 | 100 |
| N—[3-(3-benzoylpyrazolo[1,5-a]pyrimidin-7-yl)phenyl]N—(cyclopropylmethyl)acetamide | 12.5 | 100 |
| [3-[3-(2-furanylcarbonyl)pyrazolo-[1,5-a]pyrimidin-7-yl]phenyl]methylcarbamic acid, ethyl ester | 25.0 | 50 |
| [3-(3-benzoylpyrazolo[1,5-a]pyrimidin-7-yl)phenyl]methylcarbamic acid, ethyl ester | 25.0 | 100 |
| [3-(3-benzoylpyrazolo[1,5-a]pyrimidin-7-yl)phenyl]ethylcarbamic acid, ethyl ester | 25.0 | 50 |
| N—2-propenyl-N—[3-[3-(2-thienylcarbonyl)pyrazolo[1,5-a]pyrimidin-7-yl]phenyl]acetamide | 6.25 | 100 |
| N—[3-(3-benzoylpyrazolo[1,5-a]pyrimidin-7-yl)phenyl]-N—2-propenylacetamide | 3.1 | 100 |
| N—[3-[3-(2-furanylcarbonyl)pyrazolo[1,5-a]pyrimidin-7-yl]phenyl]-N—2-propenylacetamide | 25.0 | 100 |
| N—[3-[3-(4-methylbenzoyl)pyrazolo[1,5-a]pyrimidin-7-yl]phenyl]-N—2-propenylacetamide | 25.0 | 100 |
| N—[3-(3-benzoylpyrazolo[1,5-a]pyrimidin-7-yl)phenyl]-N—2-propynylacetamide | 6.25 | 100 |

Another test which has been used to assess anti-anxiety effects is a nonconditioned passive avoidance procedure described by J. R. Vogel, B. Beer and D. E. Clody, "A Simple and Reliable Conflict Procedure for Testing Anti-Anxiety Agents", Psychopharmacologia, 21, 1–7 (1971). A conflict situation is induced in rats by a modification of this method.

Groups of 6 naive, Wistar strain rats, weighing 200-240 g each were deprived of water for 48 hours and food for 24 hours. The test compounds were administered in single or graded, oral or intraperitoneal doses, suspended in a 2% starch vehicle containing 0.5% v/v polyethylene glycol and one drop of polysorbate 80. Control animals received the vehicle alone. At 30 to 60 minutes each rat was placed in an individual plexiglass chamber. Water was available ad libitum from a tap located in the rear of the chamber. A 0.7 milliampere DC shocking current was established between the stainless steel grid floor and the tap. After 20 licks of non-shocked drinking, a shock was delivered for 2 seconds and then further shocks were delivered on a ratio of one shock for 2 seconds for every 20 licks. This was continued for a total of 3 minutes. The number of shocks taken by each rat during the 3 minute interval was recorded and compared to a control group. The test compounds are considered active if the number of shocks received by the test group is significantly higher than the control group by the Mann-Witney U test. Results of this test on representative compounds of this invention appear in Table II.

TABLE II
Nonconditioned Passive Avoidance Test in Rats

| Compound | Dose (mg/kg) | Result |
|---|---|---|
| [3-[3-(2-furanylcarbonyl)pyrazolo-[1,5-a]pyrimidin-7-yl]phenyl]methylcarbamic acid, methyl ester | 1.5 | Active |
| [3-(3-benzoylpyrazolo[1,5-a]pyrimidin-7-yl)phenyl]methylcarbamic acid, methyl ester | 0.2 | Active |
| [3-(3-benzoylpyrazolo[1,5-a]pyrimidin-7-yl)phenyl]ethylcarbamic acid, methyl ester | 0.4 | Active |
| ethyl[3-[3-(2-furanylcarbonyl)pyrazolo[1,5-a]pyrimidin-7-yl]phenyl]carbamic acid, methyl ester | 0.8 | Active |
| N—[3-(3-benzoylpyrazolo[1,5-a]pyrimidin-7-yl)phenyl]-N—(cyclopropylmethyl)acetamide | 3.1 | Active |
| [3-[3-(2-furanylcarbonyl)pyrazolo-[1,5-a]pyrimidin-7-yl]phenyl]methylcarbamic acid, ethyl ester | 25.0 | Active |
| [3-(3-benzoylpyrazolo[1,5-a]pyrimidin-7-yl)phenyl]methylcarbamic acid, ethyl ester | 25.0 | Active |
| [3-(3-benzoylpyrazolo[1,5-a]pyrimidin-7-yl)phenyl]ethylcarbamic acid, ethyl ester | 25.0 | Active |
| N—2-propenyl-N—[3-[3-(2-thienylcarbonyl)pyrazolo[1,5-a]pyrimidin-7-yl]phenyl]acetamide | 3.1 | Active |
| ethyl[3-[3-(2-thienylcarbonyl)pyrazolo[1,5-a]pyrimidin-7-yl]phenyl]carbamic acid, ethyl ester | 25.0 | Active |
| N—[3-(3-benzoylpyrazolo[1,5-a]pyrimidin-7-yl)phenyl]-N—2-propenylacetamide | 0.4 | Active |
| N—[3-[3-(2-furanylcarbonyl)pyrazolo-[1,5-a]pyrimidin-7-yl]phenyl]-N—2-propenylacetamide | 3.1 | Active |
| N—[3-[3-(4-methylbenzoyl)pyrazolo-[1,5-a]pyrimidin-7-yl]phenyl]-N—2-propenylacetamide | 6.2 | Active |
| N—[3-(3-benzoylpyrazolo[1,5-a]pryimidin-7-yl)phenyl]-N—2-propynylacetamide | 25.0 | Active |

Another test utilized for the determination of anxiolytic activity is the measurement of the ability of test compounds to inhibit the binding of tritiated benzodiazepines to brain-specific receptors of warm-blooded animals. A modification of the method described by R. F. Squires, et al., Nature, 266, No. 21, p 732 (April 1977) and H. Mohler, et al., Science, 198, p 849 (1977) was employed.

Male albino rats (Wistar strain, weighing 150–200 g each) were obtained from Royalhart Farms. $^3$H-Methyldiazepam (79.9 Ci/mmol) and $^3$H-methyl-flunitrazepam (84.3 Ci/mmol) were obtained from New England Nuclear. The test compounds were solubilized in either dimethylformamide, acetic acid, ethanol or hydrochloric acid.

Whole cortex of rats was homogenized gently in 20 volumes of ice-cold 0.32M sucrose, centrifuged twice at 1000 g for 10 minutes and then recentrifuged at 30,000 g for 20 minutes to produce a crude $P_2$-synaptosomal fraction. The $P_2$-fraction was either: (1) resuspended in twice the original volume of hypotonic 50 mM Tris.HCl (pH 7.4), or (2) resuspended in one-half the original volume of hypotonic 10 mM Tris.HCl (pH 7.4) and frozen (−20° C.) until time of use. Frozen $P_2$ preparations were thawed and resuspended in four times the original homogenizing volume at time of assay.

The binding assay consisted of 300 μl of the $P_2$-fraction suspension (0.2–0.4 mg protein), 100 μl of test drug and 100 μl of $^3$H-diazepam (1.5 nM, final concentration) or $^3$H-flunitrazepam (1.0 nM, final concentration) which was added to 1.5 ml of 50 mM Tris.HCl (pH 7.4). Nonspecific binding controls and total binding controls received 100 μl of diazepam (3 μM, final concentration) and 100 μl of deionized water, respectively, in place of the test compound. Incubation for 30 minutes proceeded in ice and was terminated by filtration, under vacuum, through Whatman GF/C glass fiber filters. The filters were washed twice with 5 ml of ice-cold 50 mM Tris.HCl (pH 7.4) and placed in scintillation vials. After drying at 50°–60° C. for 30 minutes, 10 ml of Beckman Ready-Solv TM HP (a high performance premix scintillation cocktail, registered trademark of Beckman Instruments, Inc., Irvine, CA 92713) was added and the radioactivity determined in a scintillation counter.

Inhibition of binding was calculated by the difference between total binding and binding in the presence of test compound, divided by the total binding x 100.

The results of this test on representative compounds of the present invention are given in Table III.

TABLE III
Inhibition of the Binding of $^3$H—Benzodiazepine to Brain-Specific Receptors of Rats

| Compound | % Inhibition |
|---|---|
| [3-[3-(2-furanylcarbonyl)pyrazolo[1,5-a]-pyrimidin-7-yl]phenyl]methylcarbamic acid, methyl ester | 100 |
| [3-(3-benzoylpyrazolo[1,5-a]pyrimidin-7-yl)phenyl]methylcarbamic acid, methyl ester | 75 |
| [3-(3-benzoylpyrazolo[1,5-a]pyrimidin-7-yl)phenyl]ethylcarbamic acid, ethyl ester | 82 |
| ethyl[3-[3-(2-furanylcarbonyl)pyrazolo-[1,5-a]pyrimidin-7-yl]phenyl]carbamic acid, methyl ester | 88 |
| [3-(3-benzoylpyrazolo[1,5-a]pyrimidin-7-yl)phenyl]methylcarbamic acid, butyl ester | 67 |
| [3-[3-(2-furanylcarbonyl)pyrazolo[1,5-a]-pyrimidin-7-yl]phenyl]methylcarbamic acid, ethyl ester | 87 |
| [3-(3-benzoylpyrazolo[1,5-a]pyrimidin-7-yl)phenyl]methylcarbamic acid, ethyl ester | 69 |
| [3-(3-benzoylpyrazolo[1,5-a]pyrimidin-7-yl)phenyl]ethylcarbamic acid, ethyl ester | 95 |
| ethyl[3-[3-(2-furanylcarbonyl)pyrazolo-[1,5-a]pyrimidin-7-yl]phenyl]carbamic acid, | 94 |

TABLE III-continued

Inhibition of the Binding of $^3$H—Benzodiazepine to Brain-Specific Receptors of Rats

| Compound | % Inhibition |
|---|---|
| ethyl ester | |
| N—2-propenyl-N—[3-[3-(2-thienylcarbonyl)-pyrazolo[1,5-a]pyrimidin-7-yl]phenyl]-acetamide | 100 |
| ethyl[3-[3-(2-thienylcarbonyl)pyrazolo-[1,5-a]pyrimidin-7-yl]phenyl]carbamic acid, ethyl ester | 45 |
| N—[3-(3-benzoylpyrazolo[1,5-a]pyrimidin-7-yl)phenyl]-N—2-propenylacetamide | 97 |
| N—[3-[3-(2-furanylcarbonyl)pyrazolo[1,5-a]-pyrimidin-7-yl]phenyl]-N—2-propenylacetamide | 97 |
| N—[3-[3-(4-methylbenzoyl)pyrazolo[1,5-a]pyrimidin-7-yl]phenyl]-N—2-propenylacetamide | 97 |
| N—[3-(3-benzolypyrazolo[1,5-a]pyrimidin-7-yl)phenyl]-N—2-propynylacetamide | 84 |
| N—[3-[3-(2-furanylcarbonyl)pyrazolo[1,5-a]-pyrimidin-7-yl]phenyl]-N—2-propynylacetamide | 95 |

The novel compounds of the present invention have been found to be highly useful for drug therapy in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units are employed that a total of from about 10 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of nonvolatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned nonvolatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-alpha-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramsucular injection, the preferred concentration of active compound is 0.25 to 0.50 mg/ml of the final compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers and the like. Additionally, the active ingredient may be incorporated with the proper pharmaceutical carrier or carriers known in the art to produce a sustained-release tablet or capsule. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain one or more of the following: A binder such as gum tragacanth, acacia, corn starch or gelatin; excipients such as dicalcium phosphate; a disintegrating agent such as corn starch, potato starch, alginic acid and the like; a lubricant such as magnesium stearate; a wetting agent such as sodium lauryl sulfate and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially nontoxic in the amounts employed.

The following non-limiting examples illustrate the preparation of representative compounds of the present invention.

EXAMPLE 1

N-[3-[3-(Dimethylamino)-1-oxo-2-propenyl]phenyl]-cyclopropanecarboxamide

A mixture of 13.524 g of m-aminoacetophenone and 14.224 g of diisopropylethylamine in 300 ml of dichloromethane was stirred with cooling. An 11.45 g portion of cyclopropanecarboxylic acid chloride was added and the mixture was stirred at room temperature overnight.

The solid was collected, giving 17.30 g of N-(3-acetylphenyl)cyclopropanecarboxamide, mp 136°–137° C.

A 16.0 g portion of the above compound in 25 ml of dimethylformamide dimethylacetal was heated at reflux under argon for 8 hours, then evaporated. The residue was taken up in 200 ml of dichloromethane, passed through hydrous magnesium silicate, diluted with hexane and concentrated, giving 20.65 g of the desired compound, mp 182°–184° C.

EXAMPLE 2

N-[3-[3-(Dimethylamino)-1-oxo-2-propenyl]phenyl]formamide

A 25 ml portion of acetic anhydride was cooled at 0° C. in an ice bath. A 12.5 ml portion of formic acid was added, the mixture was heated at 50° C. for 15 minutes then cooled to 0° C., giving 9.69 g of crude mixed formicacetic anhydride. This anhydride was reacted with 13.52 g of m-aminoacetophenone, 14.21 g of diisopropylethylamine and 800 ml of dichloromethane as described in Example 1, giving 13.27 g of N-(3-acetylphenyl)formamide, mp 100°–102° C.

A 12.06 g portion of the above compound was reacted with dimethylformamide dimethylacetal as described in Example 1, giving 15.48 g of the desired compound, mp 165°–167° C.

EXAMPLE 3

N-[3-[3-(Dimethylamino)-1-oxo-2-propenyl]phenyl]-N-methylcyclopropanecarboxamide A mixture of 10.33 g of N-[3-[3-(dimethylamino)-1-oxo-2-propenyl]phenyl]cyclopropanecarboxamide and 1.92 g of 60% sodium hydride in oil in 50 ml of dimethylformamide was stirred for one hour under argon, then cooled in an ice bath. A solution of 0.81 g of methyl iodide in 10 ml of dimethylformamide was added dropwise. The mixture was then stirred at room temperature for 0.5 hour and extracted three times with hexane. The mixture was diluted with water and this mixture extracted with dichloromethane. This extract was evaporated and the residue crystallized from hexane, giving 10.17 g of the desired compound, mp 120°–122° C.

EXAMPLE 4

N-[3-[3-(Dimethylamino)-1-oxo-2-propenyl]phenyl]-N-methylcyclobutanecarboxamide

An 11.4 g portion of m-aminoacetophenone, 10.9 g of diisopropylethylamine, 10.0 g of cyclobutanecarboxylic acid chloride and 200 ml of dichloromethane were reacted as described in Example 1, giving 14.68 g of N-(3-acetylphenyl)cyclobutanecarboxamide.

A 13.0 g portion of the above compound was reacted with 20 ml of dimethylformamide dimethylacetal as described in Example 1, giving 16.20 g of N-[3-[3-(dimethylamino)-1-oxo-2-propenyl]phenyl]cyclobutanecarboxamide, mp 155°–157° C.

An 8.17 g portion of this compound was alkylated as described in Example 3, using 5.12 g of methyl iodide, giving 8.32 g of the desired compound, mp 117°–119° C.

EXAMPLE 5

[3-[3-(Dimethylamino)-1-oxo-2-propenyl]phenyl]carbamic acid, methyl ester

A mixture of m-aminoacetophenone, diisopropylethylamine, methyl chloroformate and dichloromethane was reacted as described in Example 1, giving 33.4 g of (3-acetylphenyl)carbamic acid, methyl ester.

A 15 g portion of the above compound was reacted with 35 ml of dimethylformamide dimethylacetal as described in Example 1, giving 15.90 g of the desired compound, mp 210°–211° C.

EXAMPLE 6

[3-[3-(Dimethylamino)-1-oxo-2-propenyl]phenyl]methylcarbamic acid, methyl ester

A 9.93 g portion of [3-[3-(dimethylamino)-1-oxo-2-propenyl]phenyl]carbamic acid, methyl ester was alkylated as described in Example 3, using 6.82 g of methyl iodide, giving 10.13 g of the desired compound, mp 93°–95° C.

EXAMPLE 7

[3-[3-(Dimethylamino)-1-oxo-2-propenyl]phenyl]ethylcarbamic acid, methyl ester

A 12.41 g portion of [3-[3-(dimethylamino)-1-oxo-2-propenyl]phenyl]carbamic acid methyl ester was alkylated as described in Example 3, using 9.36 g of ethyl iodide, giving 13.45 g of the desired compound, mp 95°–97° C.

EXAMPLE 8

N-(Cyclopropylmethyl)-N-[3-[3-(dimethylamino-1-oxo-2-propenyl]phenyl]acetamide

A 10.4 g portion of N-(3-acetylphenyl)acetamide was reacted with 25 ml of dimethylformamide dimethylacetal for 8 hours under argon giving N-[3-[3-(dimethylamino)-1-oxo-2-propenyl]phenyl]acetamide.

A 6.99 g portion of this compound was reacted with 1.44 g of sodium hydride (60% in oil) in 50 ml of dimethylformamide and then with 4.57 g of bromomethylcyclopropane in 10 ml of dimethylformamide, giving 7.55 g of the desired compound, mp 112°–114° C.

EXAMPLE 9

[3-[3-(Dimethylamino)-1-oxo-2-propenyl]phenyl]carbamic acid, butyl ester

A mixture of 27.03 g of m-aminoacetophenone, 25.85 g of diisopropylethylamine, 27.32 g of n-butyl chloroformate and 300 ml of dichloromethane was reacted as described in Example 1, giving 42.10 g of (3-acetylphenyl)carbamic acid, butyl ester, mp 59°–60° C.

A 30 g portion of the above compound was reacted with 50 ml of dimethylformamide dimethylacetal as described in Example 1, giving 29.60 g of the desired compound, mp 115°–116° C.

EXAMPLE 10

[3-[3-(Dimethylamino)-1-oxo-2-propenyl]phenyl]methylcarbamic acid, butyl ester

An 11.61 g portion of [3-[3-(dimethylamino)-1-oxo-2-propenyl]phenyl]carbamic acid, butyl ester was alkylated using the procedure of Example 3 and 6.82 g of methyl iodide, giving 11.67 g of the desired compound, mp 80°–82° C.

EXAMPLE 11

[3-[3-(Dimethylamino)-1-oxo-2-propenyl]phenyl]methylcarbamic acid, ethyl ester

A mixture of 27.03 g of m-aminoacetophenone, 27.14 g of diisopropylethylamine, 22.8 g of ethylchloroformate and 300 ml of dichloromethane was reacted as described in Example 1, giving 37.9 g of (3-acetylphenyl)carbamic acid, ethyl ester.

A 30 g portion of the above compound was further reacted with 30 ml of dimethylformamide dimethylacetal as described in Example 1, giving 37.5 g of [3-[3-(dimethylamino)-1-oxo-2-propenyl]phenyl]carbamic acid, ethyl ester, mp 121°–122° C.

A 13.1 g portion of this compound was alkylated as described in Example 3, using 8.52 g of methyl iodide, giving 13.5 g of the desired compound as a viscous red-orange liquid.

EXAMPLE 12

[3-[3-(Dimethylamino)-1-oxo-2-propenyl]phenyl]ethylcarbamic acid, ethyl ester

A 13.12 g portion of [3-[3-(dimethylamino)-1-oxo-2-propenyl]phenyl]carbamic acid, ethyl ester was alkylated as described in Example 3, using 9.36 g of ethyl iodide, giving 14.3 g of the desired compound, mp 45°–50° C.

EXAMPLE 13

N-[3-[3-(Dimethylamino)-1-oxo-2-propenyl]phenyl]-N-2-propenylacetamide

N-[3-[3-(Dimethylamino)-1-oxo-2-propenyl]phenyl]acetamide was alkylated by the procedure of Example 3, using 7.26 g of allyl bromide, giving 13.34 g of the desired compound, mp 91°–94° C.

EXAMPLE 14

N-[3-[3-(Dimethylamino)-1-oxo-2-propenyl]phenyl]-N-2-propynylacetamide

The procedure of Example 13 was followed using 9.0 g of 80% propynyl bromide in toluene, giving the desired compound, mp 98°–101° C.

EXAMPLE 15

N-[3-(3-Benzoylpyrazolo[1,5-a]pyrimidin-7-yl)phenyl]propanamide

A reaction mixture of 2.46 g of N-[3-[3-(dimethylamino)-1-oxo-2-propenyl]phenylpropanamide, 1.87 g of 3-amino-4-benzoylpyrazole and 50 ml of glacial acetic acid was refluxed for 15 hours and then the solvent was removed in vacuo. The residue was partitioned between saturated aqueous sodium bicarbonate and methylene chloride. The organic layer was dried over anhydrous sodium sulfate and then passed through a short pad of hydrous magnesium silicate. The addition of hexane to the refluxing eluate induced crystallization. After cooling, the desired intermediate was collected, giving 2.39 g, mp 172°–174° C.

Following the general procedure of Example 15, using appropriate substituted pyrazoles and appropriate 3-dimethylamino-1-substituted-2-alken-1-ones, the intermediates of Examples 16–28, listed in Table IV, were obtained.

TABLE IV

| Ex. | Pyrazole | 3-Dimethylamino-1-substituted-2-alken-1-one | Product | MP° C. |
|---|---|---|---|---|
| 16 | 3-amino-4-furoylpyrazole | N—[3-[3-(dimethylamino)-1-oxo-2-propenyl]phenyl]propanamide | N—[3-[3-(2-furanylcarbonyl)-pyrazolo[1,5-a]pyrimidin-7-yl]phenyl]propanamide | 185–186 |
| 17 | 3-amino-4-furoylpyrazole | N—[3-[3-(dimethylamino)-1-oxo-2-propenyl]phenyl]butanamide | N—[3-[3-(2-furanylcarbonyl)-pyrazolo[1,5-a]pyrimidin-7-yl]phenyl]butanamide | 151–153 |
| 18 | 3-amino-4-furoylpyrazole | N—[3-[3-(dimethylamino)-1-oxo-2-propenyl]phenyl]acetamide | N—[3-[3-(2-furanylcarbonyl)-pyrazolo[1,5-a]pyrimidin-7-yl]phenyl]acetamide | 195–196 |
| 19 | 3-amino-4-benzoylpyrazole | N—[3-[3-(dimethylamino)-1-oxo-2-propenyl]phenyl]butanamide | N—[3-(3-benzoylpyrazolo-[1,5-a]pyrimidin-7-yl)-phenyl]butanamide | 177–178 |
| 20 | 3-amino-4-(4-methyl)-benzoylpyrazole | N—[3-[3-(dimethylamino)-1-oxo-2-propenyl]phenyl]butanamide | N—[3-[3-(4-methylbenzoyl)-pyrazolo[1,5-a]pyrimidin-7-yl]phenyl]butanamide | 132–134 |
| 21 | 3-amino-4-(4-methyl)-benzoylpyrazole | N—[3-[3-(dimethylamino)-1-oxo-2-propenyl]phenyl]propanamide | N—[3-[3-(4-methylbenzoyl)-pyrazolo[1,5-a]pyrimidin-7-yl]phenyl]propanamide | 185–187 |
| 22 | 3-amino-4-(4-methoxy)benzoylpyrazole | N—[3-[3-(dimethylamino)-1-oxo-2-propenyl]phenyl]acetamide | N—[3-[3-(4-methoxybenzoyl)-pyrazolo[1,5-a]pyrimidin-7-yl]phenyl]acetamide | 222–223 |
| 23 | 3-amino-4-(4-methyl)-benzoylpyrazole | N—[3-[3-(dimethylamino)-1-oxo-2-propenyl]phenyl]acetamide | N—[3-[3-(4-methylbenzoyl)-pyrazolo[1,5-a]pyrimidin-7-yl]phenyl]acetamide | 221–223 |
| 24 | 3-amino-4-benzoylpyrazole | N—[3-[3-(dimethylamino)-1-oxo-2-butenyl]phenyl]acetamide | N—[3-(3-benzoyl-5-methyl-pyrazolo[1,5-a]pyrimidin-7-yl]phenyl]acetamide | 200–202 |
| 25 | 3-amino-4-(4-methoxy)benzoylpyrazole | N—[3-[3-(dimethylamino)-1-oxo-2-propenyl]phenyl]propanamide | N—[3-[3-(4-methoxybenzoyl)-pyrazolo[1,5-a]pyrimidin-7-yl]phenyl]propanamide | 222–224 |
| 26 | 3-amino-4-benzoylpyrazole | N—[3-[3-(dimethylamino)-1-oxo-2-propenyl]phenyl]cyclopropanecarboxamide | N—[3-(3-benzoylpyrazolo-[1,5-a]pyrimidin-7-yl)-phenyl]cyclopropanecarboxamide | 210–212 |
| 27 | 3-amino-4-(4-fluoro)-benzoylpyrazole | N—[3-[3-(dimethylamino)-1-oxo-2-propenyl]phenyl]propanamide | N—[3-[3-(4-fluorobenzoyl)-pyrazolo[1,5-a]pyrimidin-7-yl]phenyl]propanamide | 165–167 |
| 28 | 3-amino-4-(2-fluoro)-benzoylpyrazole | N—[3-[3-(dimethylamino)-1-oxo-2-propenyl]phenyl]propanamide | N—[3-[3-(2-fluorobenzoyl)-pyrazolo[1,5-a]pyrimidin-7-yl]phenyl]propanamide | 105–135 (glass) |

EXAMPLE 29

N-[3-(3-Benzoylpyrazolo[1,5-a]pyrimidin-7-yl)phenyl]-N-methylcyclobutanecarboxamide A reaction mixture comprising 2.86 g of N-[3-[3-(dimethylamino)-1-oxo-2-propenyl]phenyl]-N-methylcyclobutanecarboxamide, 1.88 g of 3-amino-4-benzoylpyrazole and 100 ml of glacial acetic acid was refluxed for 8 hours and then the solvent was removed in vacuo. The residue was partitioned between saturated aqueous sodium bicarbonate and dichloromethane. The organic layer was dried over anhydrous sodium sulfate and then passed through a short pad of hydrous magnesium silicate. The addition of hexane to the refluxing eluate induced crystallization. After cooling, the desired product was collected, giving 3.05 g, mp 168°–170° C.

EXAMPLE 30

[3-[3-(2-Furanylcarbonyl)pyrazolo[1,5-a]pyrimidin-7-yl]phenyl]methylcarbamic acid, methyl ester A reaction mixture comprising 2.62 g of [3-[3-(dimethylamino)-1-oxo-2-propenyl]phenyl]methylcarbamic acid, methyl ester, 1.77 g of 3-amino-4-furoylpyrazole and 100 ml of glacial acetic acid was reacted as described in Example 29, giving 2.90 g of the desired product, mp 152°–154° C.

Following the procedures of Examples 29 and 30 and using appropriate reactants, the products of Examples 31–58, found in Table V, were obtained.

TABLE V

| Ex. | Pyrazole | 3-Dimethylamino-1-substituted-2-alken-1-one | Product | MP° C. |
|---|---|---|---|---|
| 31 | 3-amino-4-furoylpyrazole | N—[3-[3-(dimethylamino)-1-oxo-2-propenyl]phenyl]-N—methylcyclobutanecarboxamide | N—[3-[3-(2-furanylcarbonyl)pyrazolo[1,5-a]pyrimidin-7-yl]phenyl]-N—methylcyclobutanecarboxamide | 166–167 |
| 32 | 3-amino-4-furoylpyrazole | N—[3-[3-(dimethylamino)-1-oxo-2-propenyl]phenyl]-cyclopropanecarboxamide | N—[3-[3-(2-furanylcarbonyl)pyrazolo[1,5-a]pyrimidin-7-yl]phenyl]cyclopropanecarboxamide | 227–230 |
| 33 | 3-amino-4-benzoylpyrazole | N—[3-[3-(dimethylamino)-1-oxo-2-propenyl]phenyl]-formamide | N—[3-(3-benzoylpyrazolo-[1,5-a]pyrimidin-7-yl)-phenyl]formamide | 179–182 |
| 34 | 3-amino-4-benzoylpyrazole | N—[3-(3-dimethylamino)-1-oxo-2-propenyl)phenyl]-N—methylcyclopropanecarboxamide | N—[3-(3-benzoylpyrazolo-[1,5-a]pyrimidin-7-yl)-phenyl]-N—methylcyclopropanecarboxamide | 168–170 |
| 35 | 3-amino-4-furoylpyrazole | N—[3-(3-dimethylamino)-1-oxo-2-propenyl)phenyl]-N—methylcyclopropanecarboxamide | N—[3-[3-(2-furanylcarbonyl)pyrazolo[1,5-a]pyrimidin-7-yl]phenyl]-N—methylcyclopropanecarboxamide | 207–209 |
| 36 | 3-amino-4-furoylpyrazole | [3-[3-(dimethylamino)-1-oxo-2-propenyl]phenyl]-carbamic acid, methyl ester | N—[3-[3-(2-furanylcarbonyl)pyrazolo[1,5-a]pyrimidin-7-yl]phenyl]carbamic acid, methyl ester | 206–208 |
| 37 | 3-amino-4-benzoylpyrazole | [3-[3-(dimethylamino)-1-oxo-2-propenyl]phenyl]-carbamic acid, methyl ester | [3-(3-benzoylpyrazolo-[1,5-a]pyrimidin-7-yl)-phenyl]carbamic acid, methyl ester | 196–197 |
| 38 | 3-amino-4-benzoylpyrazole | [3-[3-(dimethylamino)-1-oxo-2-propenyl]phenyl]-methylcarbamic acid, methyl ester | [3-(3-benzoylpyrazolo-[1,5-a]pyrimidin-7-yl)-phenyl]methylcarbamic acid, methyl ester | 160–162 |
| 39 | 3-amino-4-benzoylpyrazole | [3-[3-(dimethylamino)-1-oxo-2-propenyl]phenyl]-ethylcarbamic acid, methyl ester | [3-(3-benzoylpyrazolo-[1,5-a]pyrimidin-7-yl)-phenyl]ethylcarbamic acid, methyl ester | 164–166 |
| 40 | 3-amino-4-furoylpyrazole | [3-[3-(dimethylamino)-1-oxo-2-propenyl]phenyl]-ethylcarbamic acid, methyl ester | ethyl[3-[3-(2-furanylcarbonyl)pyrazolo[1,5-a]pyrimidin-7-yl]phenyl]carbamic acid, methyl ester | 162–164 |
| 41 | 3-amino-4-furoylpyrazole | [3-[3-(dimethylamino)-1-oxo-2-propenyl]phenyl]-carbamic acid, butyl ester | [3-[3-(2-furanylcarbonyl)-pyrazolo[1,5-a]pyrimidin-7-yl]phenyl]carbamic acid, butyl ester | 166–167 |
| 42 | 3-amino-4-benzoylpyrazole | N—(cyclopropylmethyl)-N—[3-[3-(dimethylamino)-1-oxo-2-propenyl]phenyl]-acetamide | N—[3-(3-benzoylpyrazolo-[1,5-a]pyrimidin-7-yl)-phenyl]-N—(cyclopropylmethyl)acetamide | 125–126 |
| 43 | 3-amino-4-furoylpyrazole | N—(cyclopropylmethyl)-N—[3-[3-(dimethylamino)-1-oxo-2-propenyl]phenyl]-acetamide | N—(cyclopropylmethyl)-N—[3-[3-(2-furanylcarbonyl)-pyrazolo[1,5-a]pyrimidin-7-yl]phenyl]acetamide | 175–176 |
| 44 | 3-amino-4-benzoylpyrazole | [3-[3-(dimethylamino)-1-oxo-2-propenyl]phenyl]-carbamic acid, butyl ester | [3-(3-benzoylpyrazolo-[1,5-a]pyrimidin-7-yl)-phenyl]carbamic acid, butyl ester | 127–129 |
| 45 | 3-amino-4-furoylpyrazole | [3-[3-(dimethylamino)-1-oxo-2-propenyl]phenyl]-methylcarbamic acid, butyl ester | [3-[3-(2-furanylcarbonyl)-pyrazolo[1,5-a]-pyrimidin-7-yl]phenyl]methylcarbamic acid, butyl ester | 122–123 |
| 46 | 3-amino-4-benzoylpyrazole | [3-[3-(dimethylamino)-1-oxo-2-propenyl]phenyl]- | [3-(3-benzoylpyrazolo-[1,5-a]pyrimidin-7-yl)- | 83–85 |

TABLE V-continued

| Ex. | Pyrazole | 3-Dimethylamino-1-substituted-2-alken-1-one | Product | MP° C. |
|---|---|---|---|---|
| | | methylcarbamic acid, butyl ester | phenyl]methylcarbamic acid, butyl ester | |
| 47 | 3-amino-4-(2-thienyl-carbonyl)pyrazole | N—[3-(3-dimethylamino)-1-oxo-2-propenyl]phenyl]-N—methylcyclopropanecarboxamide | N—methyl-N—[3-[3-(2-thienyl-carbonyl)pyrazolo[1,5-a]-pyrimidin-7-yl)phenyl]cyclo-propanecarboxamide | 201–202 |
| 48 | 3-amino-4-furoyl-pyrazole | [3-[3-(dimethylamino)-1-oxo-2-propenyl]phenyl]-methylcarbamic acid, ethyl ester | [3-[3-(2-furanylcarbonyl)-pyrazolo[1,5-a]pyrimidin-7-yl]phenyl]methylcarbamic acid, ethyl ester | 146–148 |
| 49 | 3-amino-4-benzoyl-pyrazole | [3-[3-(dimethylamino)-1-oxo-2-propenyl]phenyl]-methylcarbamic acid, ethyl ester | [3-(3-benzoylpyrazolo-[1,5-a]pyrimidin-7-yl)-phenyl]methylcarbamic acid, ethyl ester | 137–139 |
| 50 | 3-amino-4-benzoyl-pyrazole | [3-[3-(dimethylamino)-1-oxo-2-propenyl]phenyl]-ethylcarbamic acid, ethyl ester | [3-(3-benzoylpyrazolo-[1,5-a]pyrimidin-7-yl)-phenyl]ethylcarbamic acid, ethyl ester | 128–130 |
| 51 | 3-amino-4-furoyl-pyrazole | [3-[3-(dimethylamino)-1-oxo-2-propenyl]phenyl]-ethylcarbamic acid, ethyl ester | ethyl[3-[3-(2-furanylcar-bonyl)pyrazolo[1,5-a]pyrimi-din-7-yl]phenyl]carbamic acid, ethyl ester | 146–147 |
| 52 | 3-amino-4-(2-thienyl-carbonyl)pyrazole | N—[3-[3-(dimethylamino)-1-oxo-2-propenyl]phenyl]-N—2-propenylacetamide | N—2-propenyl-N—[3-[3-(2-thienylcarbonyl)pyrazolo-[1,5-a]pyrimidin-7-yl]-phenyl]acetamide | |
| 53 | 3-amino-4-(2-thienyl-carbonyl)pyrazole | [3-[3-(dimethylamino)-1-oxo-2-propenyl]phenyl]-ethylcarbamic acid, ethyl ester | ethyl[3-[3-(2-thienylcarbon-yl)pyrazolo[1,5-a]pyrimidin-7-yl]phenyl]carbamic acid, ethyl ester | 188–190 |
| 54 | 3-amino-4-benzoyl-pyrazole | N—[3-[3-(dimethylamino)-1-oxo-2-propenyl]phenyl]-N—2-propenylacetamide | N—[3-(3-benzoylpyrazolo-[1,5-a]pyrimidin-7-yl)-phenyl]-N—2-propenylacet-amide | 108–110 |
| 55 | 3-amino-4-furoyl-pyrazole | N—[3-[3-(dimethylamino)-1-oxo-2-propenyl]phenyl]-N—2-propenylacetamide | N—[3-[3-(2-furanylcarbonyl)-pyrazolo[1,5-a]pyrimidin-7-yl]phenyl]-N—2-propenyl-acetamide | 156–158 |
| 56 | 3-amino-4-(4-methyl)-benzoylpyrazole | N—[3-[3-(dimethylamino)-1-oxo-2-propenyl]phenyl]-N—2-propenylacetamide | N—[3-[3-(4-methylbenzoyl)-pyrazolo[1,5-a]pyrimidin-7-yl]phenyl]-N—2-propenylacet-amide | |
| 57 | 3-amino-4-benzoyl-pyrazole | N—[3-[3-(dimethylamino)-1-oxo-2-propenyl]phenyl]-N—2-propynylacetamide | N—[3-(3-benzoylpyrazolo-[1,5-a]pyrimidin-7-yl)-phenyl]-N—2-propynylacet-amide | 145–147 |
| 58 | 3-amino-4-furoyl-pyrazole | N—[3-[3-(dimethylamino)-1-oxo-2-propenyl]phenyl]-N—2-propynylacetamide | N—[3-[3-(2-furanylcarbonyl)-pyrazolo[1,5-a]pyrimidin-7-yl]phenyl]-N—2-propynyl-acetamide | 172–174 |

EXAMPLE 59

N-[3-[3-(2-Furanylcarbonyl)pyrazolo[1,5-a]pyrimidin-7-yl]phenyl]-N-methylcyclopropanecarboxamide To a 3.85 g sample of N-[3-[3-(2-furanylcarbonyl)pyrazolo[1,5-a]pyrimidin-7-yl]phenyl]cyclopropanecarboxamide in 40 ml of dimethylformamide is added 0.384 g of 60% sodium hydride in oil. The mixture is stirred at room temperature under argon for one hour and then 0.65 ml of methyl iodide is added. After stirring overnight at room temperature, several drops of acetic acid are added, the mixture poured onto ice-water and extracted with dichloromethane. The extracts are washed with water, dried over sodium sulfate and the solvent removed under reduced pressure. The residue is dissolved in dichloromethane, filtered through a short pad of hydrous magnesium silicate and the pad washed with dichloromethane. The filtrate is concentrated and hexane added. Cooling gives the desired product as crystals, mp 207°–209° C.

EXAMPLE 60

N-[3-(3-Benzoylpyrazolo[1,5-a]pyrimidin-7-yl)phenyl]-N-methylcyclobutanecarboxamide As described for Example 59, 0.01 mole of N-[3-(3-benzoylpyrazolo[1,5-a]pyrimidin-7-yl)phenyl]cyclobutanecarboxamide in 40 ml of dimethylformamide is reacted with 0.384 g of 60% sodium hydride in oil and then with 0.65 ml of methyl iodide to give the desired product as crystals, mp 168°–170° C.

EXAMPLE 61

N-[3-[3-(2-Furanylcarbonyl)pyrazolo[1,5-a]pyrimidin-7-yl]phenyl]-N-methylcyclobutanecarboxamide As described for Example 59, 0.01 mole of N-[3-[3-(2-furanylcarbonyl)pyrazolo[1,5-a]pyrimidin-7-yl]phenyl]cyclobutanecarboxamide in 40 ml of dimethylformamide is reacted with 0.384 g of 60% sodium hydride in oil and then with 0.65 ml of methyl iodide to give the desired product as crystals, mp 166°–167° C.

EXAMPLE 62

N-[3-(3-Benzoylpyrazolo[1,5-a]pyrimidin-7-yl)phenyl]-N-ethylformamide

As described for Example 59, 0.01 mole of N-[3-(3-benzoylpyrazolo[1,5-a]pyrimidin-7-yl)phenyl]formamide in 30 ml of dimethylformamide is reacted with 0.384 g of 60% sodium hydride in oil. To the mixture is added 0.85 ml of ethyl iodide and the mixture stirred overnight. Work up as for Example 59 gives the desired product.

EXAMPLE 63

[3-[3-(2-Furanylcarbonyl)pyrazolo[1,5-a]pyrimidin-7-yl]phenyl]methylcarbamic acid, methyl ester As described for Example 59, 0.01 mole of N-[3-[3-(2-furanylcarbonyl)pyrazolo[1,5-a]pyrimidin-7-yl]phenyl]carbamic acid, methyl ester in 50 ml of dimethylformamide is reacted with 0.384 g of 60% sodium hydride in oil and then with 0.65 ml of methyl iodide to give the desired product as crystals, mp 152°–154° C.

EXAMPLE 64

[3-(3-Benzoylpyrazolo[1,5-a]pyrimidin-7-yl)phenyl]methylcarbamic acid, methyl ester As described for Example 59, 0.01 mole of [3-(3-benzoylpyrazolo[1,5-a]pyrimidin-7-yl)phenyl]carbamic acid, methyl ester in 40 ml of dimethylformamide is reacted with 0.384 g of 60% sodium hydride in oil and then with 0.65 ml of methyl iodide to give the desired product as crystals, mp 160°–162° C.

EXAMPLE 65

[3-(3-Benzoylpyrazolo[1,5-a]pyrimidin-7-yl)phenyl]ethylcarbamic acid, methyl ester As described for Example 59, 0.01 mole of [3-(3-benzoylpyrazolo[1,5-a]pyrimidin-7-yl)phenyl]carbamic acid, methyl ester in 40 ml of dimethylformamide is reacted with 0.384 g of 60% sodium hydride in oil and then with 0.85 ml of ethyl iodide to give the desired product as crystals, mp 164°–166° C.

EXAMPLE 66

N-Methyl-N-[3-[3-(2-thienylcarbonyl)pyrazolo[1,5-a]pyrimidin-7-yl]phenyl]cyclopropanecarboxamide As described for Example 59, 0.01 mole of N-[3-[3-(2-thienylcarbonyl)pyrazolo[1,5-a]pyrimidin-7-yl]phenyl]cyclopropanecarboxamide in 40 ml of dimethylformamide is reacted with 0.384 g of 60% sodium hydride in oil and then with 0.65 ml of methyl iodide to give the desired product as crystals, mp 201°–202° C.

EXAMPLE 67

[3-(3-Benzoylpyrazolo[1,5-a]pyrimidin-7-yl)phenyl]methylcarbamic acid, ethyl ester As described for Example 59, 0.01 mole of [3-(3-benzoylpyrazolo[1,5-a]pyrimidin-7-yl)phenyl]carbamic acid, ethyl ester in 40 ml of dimethylformamide is reacted with 0.384 g of 60% sodium hydride in oil and then with 0.65 ml of methyl iodide to give the desired product as crystals, mp 137°–139° C.

EXAMPLE 68

Ethyl[3-[3-(2-furanylcarbonyl)pyrazolo[1,5-a]pyrimidin-7-yl]phenyl]carbamic acid, methyl ester As described for Example 59, 0.01 mole of 3-[3-(2-furanylcarbonyl)pyrazolo[1,5-a]pyrimidin-7-yl]phenyl]carbamic acid, methyl ester in 40 ml of dimethylformamide is reacted with 0.384 g of 60% sodium hydride in oil and then with 0.85 ml of ethyl iodide to give the desired product as crystals, mp 162°–164° C.

EXAMPLE 69

[3-(3-Benzoylpyrazolo[1,5-a]pyrimidin-7-yl)phenyl]methylcarbamic acid, butyl ester As described for Example 59, 0.01 mole of [3-(3-benzoylpyrazolo[1,5-a]pyrimidin-7-yl)phenyl]carbamic acid, butyl ester in 40 ml of dimethylformamide is reacted with 0.384 g of 60% sodium hydride and then with 0.65 ml of methyl iodide to give the desired product as crystals, mp 83°–85° C.

EXAMPLE 70

[3-(3-Benzoylpyrazolo[1,5-a]pyrimidin-7-yl)phenyl]ethylcarbamic acid, ethyl ester As described for Example 59, 0.01 mole of [3-(3-benzoylpyrazolo[1,5-a]pyrimidin-7-yl)phenyl]carbamic acid, ethyl ester in 30 ml of dimethylformamide is reacted with 0.384 g of 60% sodium hydride in oil and then with 0.85 ml of ethyl iodide to give the desired product as crystals, mp 128°–130° C.

EXAMPLE 71

[3-[3-(2-Thienylcarbonyl)pyrazolo[1,5-a]pyrimidin-7-yl]phenyl]propenylcarbamic acid, ethyl ester As described for Example 59, 0.01 mole of [3-[3-(2-thienylcarbonyl)pyrazolo[1,5-a]pyrimidin-7-yl]phenyl]carbamic acid, ethyl ester in 40 ml of dimethylformamide is reacted with 0.384 g of 60% sodium hydride in oil and then with 0.87 ml of 3-bromopropene to give the desired product.

EXAMPLE 72

[3-(3-Benzoylpyrazolo[1,5-a]pyrimidin-7-yl)phenyl]-N-2-propenylcarbamic acid, ethyl ester As described for Example 59, 0.01 mole of [3-(3-benzoylpyrazolo[1,5-a]pyrimidin-7-yl)phenyl]carbamic acid, ethyl ester in 30 ml of dimethylformamide is reacted with 0.384 g of 60% sodium hydride in oil and then with 0.87 ml of 3-bromopropene to give the desired product.

EXAMPLE 73

[3-(3-Benzoylpyrazolo[1,5-a]pyrimidin-7-yl)phenyl]-N-2-propynylcarbamic acid, ethyl ester As described for Example 59, 0.01 mole of [3-(3-benzoylpyrazolo[1,5-a]pyrimidin-7-yl)phenyl]carbamic acid, ethyl ester in 40 ml of dimethylformamide is reacted with 0.384 g of 60% sodium hydride in oil and then with 0.80 ml of 3-bromopropyne to give the desired product.

EXAMPLE 74

[3-[3-(2-Furanylcarbonyl)pyrazolo[1,5-a]pyrimidin-7-yl]phenyl]-N-2-propenylcarbamic acid, ethyl ester A mixture of 0.01 mole of N-[3-[3-(dimethylamino)-1-oxo-2-propenyl]phenyl]-N-2-propenylcarbamic acid, ethyl ester and 0.01 mole of 3-amino-4-furoylpyrazole in 50 ml of glacial acetic acid is refluxed for 12 hours and the solvent removed in vacuo. The residue is partitioned between aqueous sodium bicarbonate and dichloromethane. The organic layer is separated, dried over anhydrous sodium sulfate and passed through a 2–3 cm thick layer of hydrous magnesium silicate. The filter cake is washed with 2–3 volumes of additional dichloromethane and the filtrate concentrated. Addition of hexane and concentration gives the desired product.

EXAMPLE 75

N-[3-[3-(4-Methylbenzoyl)pyrazolo[1,5-a]pyrimidin-7-yl]phenyl]-N-2-propenylpropanamide As described for Example 59, 0.01 mole of N-[3-[3-(4-methylbenzoyl)pyrazolo[1,5-a]pyrimidin-7-yl]phenyl-propanamide in 40 ml of dimethylformamide is reacted with 0.384 g of 60% sodium hydride in oil and then with 0.87 ml of 3-bromopropene to give the desired product.

EXAMPLE 76

N-[3-[3-(4-Methoxybenzoyl)pyrazolo[1,5-a]pyrimidin-7-yl]phenyl]-N-2-propynylacetamide As described for Example 59, 0.01 mole of N-[3-[3-(4-methoxybenzoyl)pyrazolo[1,5-a]pyrimidin-7-yl]phenyl-]acetamide in 40 ml of dimethylformamide is reacted with 0.384 g of 60% sodium hydride in oil and then with 0.80 ml of 3-bromopropyne to give the desired product.

EXAMPLE 77

N-[3-[3-(4-Methylbenzoyl)pyrazolo[1,5-a]pyrimidin-7-yl]phenyl]-N-2-propynylacetamide As described for Example 59, 0.01 mole of N-[3-[3-(4-methylbenzoyl)pyrazolo[1,5-a]pyrimidin-7-yl]phenyl-]acetamide in 40 ml of dimethylformamide is reacted with 0.384 g of 60% sodium hydride in oil and then with 0.80 ml of 3-bromopropyne to give the desired product.

EXAMPLE 78

N-[3-[3-(4-Fluorobenzoyl)pyrazolo[1,5-a]pyrimidin-7-yl]phenyl]-N-2-propenylpropanamide As described for Example 59, 0.01 mole of N-[3-[3-(4-fluorobenzoyl)pyrazolo[1,5-a]pyrimidin-7-yl]phenyl]-propanamide in 40 ml of dimethylformamide is reacted with 0.384 g of 60% sodium hydride in oil and then with 0.87 ml of 3-bromopropene to give the desired product.

EXAMPLE 79

N-[3-[3-(2-Fluorobenzoyl)pyrazolo[1,5-a]pyrimidin-7-yl]phenyl]-N-2-propynylpropanamide As described for Example 59, 0.01 mole of N-[3-[3-(2-fluorobenzoyl)pyrazolo[1,5-a]pyrimidin-7-yl]phenyl]-propanamide in 30 ml of dimethylformamide is reacted with 0.384 g of 60% sodium hydride in oil and then with 0.80 ml of 3-bromopropyne to give the desired product.

EXAMPLE 80

N-[3-(3-Benzoylpyrazolo[1,5-a]pyrimidin-7-yl)phenyl]-N,4-dimethylbenzenesulfonamide A mixture consisting of 7.2 g of N-[3-(3-dimethylamino)-1-oxo-2-propenyl]phenyl]-N,4-dimethyl-benzenesulfonamide, 3.8 g of (3-amino-1N-pyrazol-4-yl)phenyl methanone, and 100 ml of glacial acetic acid were combined and heated at the boiling point under reflux for 18 hours. The hot solution was diluted with 100 ml of glacial acetic acid and cooled to room temperature, whereupon a precipitate formed. It was collected, washed with 300 ml of saturated aqueous sodium bicarbonate solution, then 200 ml of water, and air dried. Recrystallization from 100 ml of 2-methoxyethanol gave 5.1 g of the desired compound, mp 170°–171° C.

EXAMPLE 81

[7-[3-(Methylamino)phenyl]pyrazolo[1,5-a]pyrimidin-3-yl]phenyl methanone

Five grams of N-[3-(3-benzoylpyrazolo[1,5-a]pyrimidin-7-yl)phenyl]-N,4-dimethylbenzenesulfonamide was added to a mixture of 50 ml of trifluoroacetic acid and 10 ml of concentrated sulfuric acid. This mixture was heated at the boiling point under reflux for 3 hours. It was then poured onto 300 g of ice containing 150 ml of 10N sodium hydroxide solution. The yellow precipitate that formed was collected, washed with water, and air dried. It was dissolved in 100 ml of methylene chloride, the solution dried over magnesium sulfate, and the methylene chloride was then removed in vacuo. A bright yellow residue of 3.4 g of the desired compound was left, mp 134°–136° C.

EXAMPLE 82

N-[3-(3-Benzoylpyrazolo[1,5-a]pyrimidin-7-yl)phenyl]-2-dimethylamino-N-methylacetamide A suspension of 1.7 g of N-[3-(3-benzoylpyrazolo[1,5-a]pyrimidin-7-yl)phenyl]-2-bromo-N-methylacetamide in 100 ml of ethanol was treated with gaseous dimethylamine until a solution resulted. This was then placed in a pressure bottle and kept at room temperature for 16 hours. The ethanol was removed in vacuo and the residue partitioned between 50 ml of saturated aqueous sodium bicarbonate solution and 100 ml of methylene chloride. The methylene chloride layer was separated, dried over magnesium sulfate, and the methylene chloride removed in vacuo. The residue was dissolved in 50 ml of methylene chloride, the solution then treated with hexane at the boiling point until turbidity was present. Cooling at −10° C. gave a low yield of tacky solid. The cold mixture was treated with activated charcoal, clarified and the filtrate again treated at the boiling point with hexane until turbidity occurred. Cooling at −10° C. gave 0.3 g of the desired compound as a bright yellow solid, mp 166°–168° C.

EXAMPLE 83

N-[3-(3-Benzoylpyrazolo[1,5-a]pyrimidin-7-yl)phenyl]-2-bromo-N-methylacetamide

Three grams of [7-[3-(methylamino)phenyl]-pyrazolo[1,5-a]pyrimidin-3-yl]phenyl methanone was dissolved in 150 ml of tetrahydrofuran. The solution was stirred as 2 ml of diisopropylethylamine, and then 2.3 g of bromoacetyl bromide were added. A precipitate formed immediately. The mixture was stirred at room temperature for 18 hours. A 150 ml portion of water was then added, the mixture heated until solution occurred, and then cooled at −10° C. A precipitate of the desired compound was obtained. It was collected, washed with water, and dried at 60° C. in vacuo giving 1.7 g, mp 175°–177° C.

What is claimed is:

1. A compound selected from those of the formula:

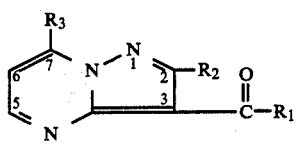

wherein

R$_1$ is selected from the group consisting of unsubstituted phenyl; phenyl mono- or disubstituted by halogen, alkyl(C$_1$-C$_3$) or alkoxy(C$_1$-C$_3$); phenyl monosubstituted by trifluoromethyl, alkylthio(C$_1$-C$_3$), alkylamino(C$_1$-C$_3$), dialkylamino(C$_1$-C$_3$), methylenedioxy, alkylsulfonyl(C$_1$-C$_3$) or alkanoylamino(C$_1$-C$_3$); naphthalenyl; thiazolyl; biphenyl; thienyl; furanyl; pyridinyl; substituted thiazolyl; substituted biphenyl; substituted thienyl; and substituted pyridinyl, wherein the substituents are selected from one or two of the groups consisting of halogen, alkyl(C$_1$-C$_3$) and alkoxy(C$_1$-C$_3$);

R$_2$ is selected from the group consisting of hydrogen and alkyl(C$_1$-C$_3$);

R$_3$ is

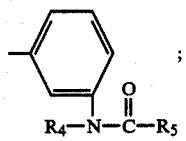

R$_4$ is selected from the group consisting of hydrogen, alkenyl(C$_2$-C$_6$), —CH$_2$C≡CH, cycloalkyl(C$_3$-C$_6$-)methyl, —CH$_2$OCH$_3$ and —CH$_2$CH$_2$OCH$_3$; and R$_5$ is selected from the group consisting of hydrogen, cycloalkyl(C$_3$-C$_6$), —O—alkyl(C$_1$-C$_6$), —N—H—alkyl(C$_1$-C$_3$), —N—dialkyl(C$_1$-C$_3$), —(CH$_2$)$_n$—O—alkyl(C$_1$-C$_3$), —(CH$_2$)$_n$—NH—alkyl(C$_1$-C$_3$), —(CH$_2$)$_n$—N—dialkyl(C$_1$-C$_3$), where n is an integer 1-3 inclusive, and R$_5$ may be alkyl(C$_1$-C$_6$), when R$_4$ is not hydrogen.

2. A compound according to claim 1, wherein R$_1$ is selected from the group consisting of unsubstituted phenyl; phenyl mono-substituted by halogen, alkyl(C$_1$-C$_3$), alkoxy(C$_1$-C$_3$) or trifluoromethyl; thienyl; furanyl; and pyridinl; R$_2$ is hydrogen; R$_4$ is selected from the group consisting of alkenyl(C$_2$-C$_6$) and —CH$_2$—C≡CH; and R$_5$ is selected from the group consisting of cycloalkyl(C$_3$-C$_6$); —O—alkyl(C$_1$-C$_6$); —N—dialkyl(C$_1$-C$_3$); and, when R$_4$ is not hydrogen, alkyl(C$_1$-C$_6$).

3. The compound according to claim 2, N-[3-(3-benzoylpyrazolo[1,5-a]pyrimidin-7-yl)phenyl]-N-methylcyclobutanecarboxamide.

4. The compound according to claim 2, N-[3-(3-benzoylpyrazolo[1,5-a]pyrimidin-7-yl)phenyl]-N-methylcyclopropanecarboxamide.

5. The compound according to claim 2, [3-(3-benzoylpyrazolo[1,5-a]pyrimidin-7-yl)phenyl]methylcarbamic acid, methyl ester.

6. The compound according to claim 2, [3-(3-benzoylpyrazolo[1,5-a]pyrimidin-7-yl)phenyl]ethylcarbamic acid, methyl ester.

7. The compound according to claim 2, N-methyl-N-[3-[3-(2-thienylcarbonyl)pyrazolo[1,5-a]pyrimidin-7-yl]phenyl]cyclopropanecarboxamide.

8. The compound according to claim 2, [3-(3-benzoylpyrazolo[1,5-a]pyrimidin-7-yl)phenyl]methylcarbamic acid, methyl ester.

9. The compound according to claim 2, [3-(3-benzoylpyrazolo[1,5-a]pyrimidin-7-yl)phenyl]ethylcarbamic acid, ethyl ester.

10. The compound according to claim 2, N-2-propenyl-N-[3-[3-(2-thienylcarbonyl)pyrazolo[1,5-a]pyrimidin-7-yl]phenyl]acetamide.

11. The compound according to claim 2, ethyl[3-[3-(2-thienylcarbonyl)pyrazolo[1,5-a]pyrimidin-7-yl]phenyl]carbamic acid, ethyl ester.

12. The compound according to claim 2, N-[3-(3-benzoylpyrazolo[1,5-a]pyrimidin-7-yl)phenyl]-N-2-propenylacetamide.

13. The compound according to claim 2, N-[3-(3-benzoylpyrazolo[1,5-a]pyrimidin-7-yl)phenyl]-N-2-propynylacetamide.

14. A method of ameliorating anxiety in a mammal which comprises administering an amount of a compound of claim 1 sufficient to relieve anxiety.

15. A composition of matter in dosage unit form comprising from 2–750 mg of a compound of claim 1 in association with a pharmaceutically acceptable carrier.

* * * * *